United States Patent
Drnevich et al.

(10) Patent No.: US 9,290,422 B2
(45) Date of Patent: Mar. 22, 2016

(54) HYBRID PLANT FOR LIQUID FUEL PRODUCTION

(71) Applicants: Raymond F. Drnevich, Clarence Center, NY (US); Shrikar Chakravarti, East Amherst, NY (US); Minish M. Shah, East Amherst, NY (US)

(72) Inventors: Raymond F. Drnevich, Clarence Center, NY (US); Shrikar Chakravarti, East Amherst, NY (US); Minish M. Shah, East Amherst, NY (US)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 464 days.

(21) Appl. No.: 13/686,328

(22) Filed: Nov. 27, 2012

(65) Prior Publication Data

US 2014/0148519 A1    May 29, 2014

(51) Int. Cl.
*C07C 27/00* (2006.01)
*C07C 1/12* (2006.01)
(Continued)

(52) U.S. Cl.
CPC . *C07C 1/12* (2013.01); *C01B 3/382* (2013.01); *C07C 29/1518* (2013.01); *C10G 2/30* (2013.01); *C10K 1/003* (2013.01); *C10K 1/005* (2013.01); *C10K 3/06* (2013.01); *C01B 2203/0233* (2013.01); *C01B 2203/0244* (2013.01); *C01B 2203/0283* (2013.01); *C01B 2203/043* (2013.01);
(Continued)

(58) Field of Classification Search
CPC .............. C01B 2203/1258; C01B 2203/0233; C01B 2203/148; C01B 2203/0244; C01B 2203/062; C01B 2203/0811; C01B 2203/142; C07C 29/1518; C07C 1/12; C07C 31/04; C10G 2/30; C10J 2300/1665; C10J 2300/1838; C10J 2300/1815; C10J 2300/1659; C10J 3/721; C10K 1/003; C10K 3/06
USPC .......................... 518/700, 702, 703, 704, 705
See application file for complete search history.

(56) References Cited

U.S. PATENT DOCUMENTS 3,972,958 A    8/1976    Garwood et al.
4,407,973 A    10/1983    Van Dijk et al.
(Continued)

FOREIGN PATENT DOCUMENTS

EP    0342610 A2    11/1989
WO    WO99/55618    11/1999
(Continued)

OTHER PUBLICATIONS

"Survey and Down-Selection of Acid Gas Removal Systems for the Thermochemical Conversion of Biomass to Ethanol with a Detailed Analysis of an MDEA System", Task 1: Acid Gas Removal Technology Survey and Screening for Thermochemical Ethanol Synthesis; Task 2: Detailed MDEA Process Analysis National Renewable Energy Laboratory, Subcontract Report: NREL/SR-5100-50482 (May 2011).

(Continued)

*Primary Examiner* — Jafar Parsa
(74) *Attorney, Agent, or Firm* — Iurie A. Schwartz (57) ABSTRACT

A hybrid plant and method for producing liquid fuel product from hydrogen and carbon monoxide containing streams produced by gasifying solid carbonaceous feedstock and steam reforming of light fossil fuels. When a gasification unit in the hybrid plant is operating at reduced capacity or is not operational, oxygen that would have been used in the gasification unit is diverted to a light fossil fuel conversion unit containing an autothermal reformer to increase $H_2$-rich syngas flow to a liquid fuel production unit and maintain liquid fuel production at near nameplate capacity.

12 Claims, 3 Drawing Sheets

(51) Int. Cl.

| | |
|---|---|
| *C07C 29/151* | (2006.01) |
| *C10K 3/06* | (2006.01) |
| *C10G 2/00* | (2006.01) |
| *C10K 1/00* | (2006.01) |
| *C01B 3/38* | (2006.01) |
| *C10J 3/72* | (2006.01) |
| *C10K 3/04* | (2006.01) |

(52) U.S. Cl.
CPC ... *C01B 2203/0475* (2013.01); *C01B 2203/062* (2013.01); *C01B 2203/0811* (2013.01); *C01B 2203/1241* (2013.01); *C01B 2203/1258* (2013.01); *C01B 2203/142* (2013.01); *C01B 2203/148* (2013.01); *C10J 3/721* (2013.01); *C10J 2300/1659* (2013.01); *C10J 2300/1665* (2013.01); *C10J 2300/1678* (2013.01); *C10J 2300/1815* (2013.01); *C10J 2300/1838* (2013.01); *C10K 3/04* (2013.01)

(56) References Cited

U.S. PATENT DOCUMENTS

| | | | |
|---|---|---|---|
| 4,443,560 | A | 4/1984 | Le Blanc, Jr. et al. |
| 4,675,344 | A | 6/1987 | Conway et al. |
| 4,775,696 | A | 10/1988 | Prada-Silva et al. |
| 4,831,060 | A | 5/1989 | Stevens et al. |
| 4,882,360 | A | 11/1989 | Stevens |
| 4,888,131 | A | 12/1989 | Goetsch et al. |
| 5,554,351 | A | 9/1996 | Primdahl |
| 6,136,577 | A | 10/2000 | Gaddy |
| 6,486,219 | B1 | 11/2002 | Janda et al. |
| 6,958,363 | B2 | 10/2005 | Espinoza et al. |
| 6,974,844 | B2 | 12/2005 | Steynberg |
| 7,008,967 | B2 | 3/2006 | Keyser et al. |
| 7,087,652 | B2 | 8/2006 | Abbott et al. |
| 7,863,341 | B2 | 1/2011 | Routier |
| 7,983,341 | B2 | 7/2011 | Wang |
| 8,106,102 | B2 | 1/2012 | Steynberg et al. |
| 2008/0306171 | A1 | 12/2008 | Van Hardeveld |
| 2009/0246118 | A1 | 10/2009 | Drnevich et al. |
| 2009/0293359 | A1 | 12/2009 | Simmons et al. |
| 2010/0113624 | A1 | 5/2010 | Routier |
| 2010/0158792 | A1 | 6/2010 | Drnevich et al. |
| 2011/0071229 | A1 | 3/2011 | Robertson et al. |
| 2011/0218254 | A1 | 9/2011 | Chakravarti et al. |
| 2012/0270957 | A1 | 10/2012 | Kresnyak |
| 2013/0079426 | A1 | 3/2013 | Ravikumar et al. |

FOREIGN PATENT DOCUMENTS

| | | |
|---|---|---|
| WO | WO2007/009984 A1 | 1/2007 |
| WO | WO2009/113006 A2 | 9/2009 |
| WO | WO2009/126769 A2 | 10/2009 |

OTHER PUBLICATIONS

Anderson, R. B. et al. "Synthesis of Alcohols by Hydrogenation of Carbon Monoxide". Industrial and Engineering Chemistry, vol. 44, No. 10. (1952) pp. 2418-2424.

Eilers, J. et al. "The Shell Middle Distillate Synthesis Process (SMDS)", J. C. Baltzer A. G., Scientific Publishing Company, Catalysis Letters 7 (1990) pp. 253-270.

Phillips, S. et al. "Thermochemical Ethanol via Indirect Gasification and Mixed Alcohol Synthesis of Lignocellulosic Biomass". Technical Report, NREL/TO-10-41168, Apr. 2007.

Reed & Gaur. "A Survey of Biomass Gasification-2001". $2^{nd}$ Edition, survey for the National Renewable Energy Laboratory (NREL) and Biomass Energy Foundation, published by Bef Press Books, 2001, Chapter 1, pp. 1-1 to 1-24 and Chapter 3, pp. 3-1 to 3-7, 3-17 to 3-26 and 3-46 to 3-51.

HYBRID PLANT FOR LIQUID FUEL PRODUCTION

BACKGROUND OF THE INVENTION

1. Field of the Invention

The present invention relates to the production of liquid fuels, and more particularly to a hybrid plant for low cost production of liquid fuels from hydrogen and carbon monoxide containing streams using light fossil fuel (for e.g. methane, natural gas, liquefied petroleum gas, naphtha), and solid feedstock such as biomass, coal, petroleum coke and the like.

2. Description of Related Art

Liquid fuels can be produced from solid feedstock materials by first gasifying the solid feedstock material to form hydrogen and carbon monoxide containing stream (gasifier-syngas) that is further treated to form desired liquid fuel product. Typically a single train gasification facility employing known gasifier technologies such as entrained flow, fixed or moving bed and fluidized bed will have an annual availability of less than 90%.

Higher gasifier availabilities are desired to increase product income to offset the capital cost of the overall project. A second and even a third gasification unit (two operating and one spare) are included in such projects to improve overall product availability and project economics. The inclusion of additional solids processing and gasification trains is capital intensive. In addition, conventional gasification systems for liquids production are generally designed with startup/auxiliary boilers to provide steam required for initiating unit operations such as feedstock drying, gasification where steam is often used as a moderator to control gasifier temperature, and regeneration of solvent used in acid gas removal system. These boilers add to the cost of the overall project.

At design conditions the gasifier-syngas produced from gasification of solid feedstock material such as coal, biomass, petroleum coke and the like typically has a molar ratio of hydrogen to carbon monoxide ($H_2$:CO) considerably less than two, and often less than one. The $H_2$:CO ratio considerably less than two is not optimal for converting gasifier-syngas into liquid fuel product such as Fischer-Tropsch liquids, methanol and the like. To improve liquid fuel product yield several options are available to adjust the $H_2$:CO ratio in the feed to the liquid fuel production unit. For example, one approach is to subject the gasifier-syngas to water gas shift reactions to first increase its $H_2$:CO ratio then convert into liquid fuel product; another approach is to mix with a hydrogen and carbon monoxide containing gas that has a higher $H_2$:CO ratio to form a mixture containing desirable $H_2$:CO ratio; yet another approach is to add hydrogen to increase $H_2$:CO ratio, yet another approach is some combination of these.

Liquid fuels can also be produced from light fossil fuels by steam methane reforming (SMR), autothermal reforming (ATR), combinations of steam methane reforming and autothermal reforming (also referred to as secondary reforming) to form a hydrogen and carbon monoxide containing stream (synthesis gas) that is further treated to form desired liquid fuel product. Typically, such a light fossil fuel conversion unit containing SMR, ATR or combination of SMR and ATR will have an annual availability of greater than 98%.

U.S. Pat. No. 4,407,973 to van Dijk et al. discloses an integrated system containing two methanol plants. The first methanol plant is designed to use a hydrogen and carbon monoxide containing gas produced by a steam methane reformer. The second methanol plant is designed to use two gases, one of which is the purge gas from the first methanol plant and the other containing hydrogen and carbon monoxide produced by high temperature partial oxidation of heavy carbonaceous fuel such as coal. The two plants are designed such that the methanol output of the integrated system when both plants are operational lies between 1.45 and 1.75 of the design capacity of the first methanol plant that employs steam methane reformer. The hydrogen and carbon monoxide containing gas from steam methane reformer fed to the first methanol plant contains hydrogen in excess of that required for methanol synthesis reactions. The excess hydrogen ends up in the purge stream, and has considerably higher hydrogen to carbon monoxide ratio than in the feed. The second methanol plant in effect is sized to utilize the purge stream in combination with hydrogen and carbon monoxide containing gas produced by high temperature partial oxidation of coal to output additional methanol between 45 and 75% of the design capacity of the first methanol plant. When the high temperature partial oxidation unit is unavailable then the integrated system output is about 57% (1/1.75) or about 69% (1/1.45) of the integrated system design capacity.

U.S. Pat. No. 4,443,560 to Le Blanc et al. discloses an integrated system containing two methanol plants. The first methanol plant is designed to use a hydrogen and carbon monoxide containing gas produced by a steam methane reformer. The purge gas from the first methanol plant is first treated in a secondary reformer by contacting with steam and oxygen in the presence of reforming catalyst and then passed on to the second methanol plant. The second methanol plant uses this treated (reformed) purge gas as well as a hydrogen and carbon monoxide containing gas produced by high temperature partial oxidation of heavy carbonaceous fuel such as coal. It also discloses that if the first methanol plant is not present or a first methanol plant is not desired then the hydrogen and carbon monoxide containing gas leaving the steam methane reformer is passed directly to a secondary reformer and treated with oxygen and steam in the presence of reforming catalyst. The effluent from the secondary reformer is cooled and subjected to condensate removal, then mixed with hydrogen and carbon monoxide containing gas produced by high temperature partial oxidation of heavy carbonaceous material such as coal. The resulting mixture is then fed to the second or the only methanol plant.

U.S. Pat. No. 7,863,341 B2 to Routier describes an integrated process for producing hydrogen and carbon monoxide containing gases from two sources to form a gas containing optimum hydrogen to carbon monoxide ratio for use as feed in the Fischer-Tropsch process. The first source such as coal, peat, bitumen has low hydrogen to carbon ratio. This first source is contacted with oxygen in a gasifier to produce syngas that has a ratio of hydrogen to carbon monoxide typically between 0.5:1 and 0.8:1. The second source such as natural gas, coal bed methane gas has high hydrogen to carbon ratio. The second source is reacted with steam in a steam methane reformer (SMR) to produce syngas that has a ratio of hydrogen to carbon monoxide typically between 5:1 and 6:1. The syngas from the gasification unit and the SMR are combined in appropriate proportions to form Fischer-Tropsch process feed gas that has a ratio of hydrogen to carbon monoxide of about two.

U.S. Publication 2011/0218254 A1 to Chakravarti et al. discloses process configurations to produce feed gas for producing Fischer-Tropsch liquids, ethanol, etc. The feed gas is formed by mixing appropriate proportions of hydrogen and carbon monoxide containing streams from gasification of solid feedstock and reforming of light fossil fuels and hydrocarbon containing byproduct streams from the liquid fuel production unit. In some configurations the effluent from the gasification of solid feedstock is subjected to partial oxidation to convert heavier hydrocarbons into at least hydrogen and carbon monoxide.

The need continues to exist for a liquid fuel production method and plant that increases product income to offset the capital cost of the overall project. It is an object of the present invention to produce liquid fuel product from hydrogen and carbon monoxide containing gas formed by converting solid feedstock using oxygen and by converting light fossil fuels using oxygen to provide improved product availability and project economics.

It is also an object of the invention to maintain liquid fuel production at near nameplate capacity under a variety of conditions, including when solid feedstock conversion unit is not operational or operating at below the nameplate capacity. Equipment utilization and productivity is maximized by maintaining the liquid fuel production within acceptable ranges of design capacity. Project cost is reduced by achieving high availability without extra equipment such as spare gasifiers.

Other objects and aspects of the present invention will become apparent to one of ordinary skill in the art upon review of the specification, drawings and claims appended hereto.

SUMMARY OF THE INVENTION

According to an aspect of the invention a method and a hybrid plant is provided for producing liquid fuel product from solid feedstock materials and light fossil fuels at near nameplate capacity under a variety of conditions.

The hybrid plant comprises a gasification unit for converting solid feedstock materials to hydrogen and carbon monoxide containing syngas from here-on referred to as gasifier-syngas, a light fossil fuel conversion unit using either an auto thermal reformer (ATR) or combination of steam methane reformer (SMR) and autothermal reformer (ATR) for converting light fossil fuels to hydrogen and carbon monoxide containing gas from here-on referred to as $H_2$-rich syngas, and a liquid fuel production unit containing Fischer-Tropsch reactor or methanol reactor or the like and associated product upgrading system for converting hydrogen and carbon monoxide containing gas into liquid fuel product. The gasification unit, the light fossil fuel conversion unit, and the liquid production unit are sized to enable production of liquid fuel product at near nameplate capacity.

The method includes: forming a hydrogen and carbon monoxide containing gasifier-syngas by gasifying solid feedstock using oxygen; forming a hydrogen and carbon monoxide containing $H_2$-rich syngas by subjecting light fossil fuels to steam reforming and partial oxidation reactions using oxygen; producing a liquid fuel product from gasifier-syngas and/or $H_2$-rich syngas wherein the $H_2$-rich syngas provides at least 50% of the hydrogen plus carbon monoxide and less than 80% of the carbon monoxide feed to the liquid fuel production unit during normal operations, that is when both gasifier-syngas and $H_2$-rich syngas are available at design flow.

When reduced amount of gasifier-syngas is available from the gasification unit in the hybrid plant, then light fossil fuel feed to the light fossil fuel conversion unit is increased; oxygen input to the autothermal reformer in the light fossil fuel conversion unit is increased by diverting at least a portion of the gasification unit oxygen feed; the light fossil fuel conversion unit steam to carbon ratio is decreased; $H_2$-rich syngas produced in the light fossil fuel conversion unit with or without mixing with gasifier-syngas from the gasification unit is fed to the liquid fuel production unit to produce a liquid fuel product at a production rate between 70% to 110% of the hybrid plant design production rate.

According to another aspect of the invention oxygen input to the autothermal reformer is increased by diverting at least 10% of the design value of the gasification unit oxygen feed.

According to yet another aspect of the invention a $CO_2$ stream is recycled to the autothermal reformer.

According to yet other aspects of the invention when reduced amount of gasifier-syngas is available from the gasification unit then one or more of following adjustments are made:
the light fossil fuel conversion unit steam to carbon ratio is decreased to a value greater than 1.8 when the light fossil fuel conversion unit contains a steam methane reformer coupled to a downstream autothermal reformer, or to a value greater than 0.4 when the light fossil fuel conversion unit contains only an autothermal reformer
the light fossil fuel feed is increased such that the autothermal reformer discharge gas flow at operating temperature and pressure (actual volumetric flow rate for e.g. actual cubic feet per hour) does not exceed a design value
the light fossil fuel feed is increased such that flow rate of $H_2$-rich syngas leaving a $CO_2$ removal unit in fluid communication with the light fossil fuel conversion unit does not exceed a design value
the oxygen input to the light fossil fuel conversion unit is increased such that the autothermal reformer discharge gas temperature does not exceed a design value
the additional light fossil fuel feed to the light fossil fuel conversion unit is introduced into an autothermal reformer
the additional light fossil fuel feed to the light fossil fuel conversion unit is introduced into a steam methane reformer coupled to a downstream autothermal reformer in the fossil fuel conversion unit
the additional light fossil fuel feed to the light fossil fuel conversion unit is divided into two streams, where the first stream is fed to a steam methane reformer coupled to a downstream autothermal reformer in the light fossil fuel conversion unit, and the second stream is fed directly to the downstream autothermal reformer
a portion of the $H_2$-rich syngas is further treated to recover hydrogen product.
the oxygen diverted from the gasification unit to the light fossil fuel conversion unit is from an air separation unit within the hybrid plant or from an air separation unit external to the hybrid plant.

BRIEF DESCRIPTION OF THE FIGURES

The objects and advantages of the invention will be better understood from the following detailed description of the preferred embodiments thereof in connection with the accompanying figures wherein like numbers denote same features throughout and wherein.

DETAILED DESCRIPTION OF THE INVENTION

The following description will refer to embodiments in which hydrogen and carbon monoxide containing streams produced from gasification of solid feed material and from reforming of light fossil fuel are further treated to produce liquid fuels such as alcohols, Fischer Tropsch liquids, gasoline, diesel and the like.

As used herein, "solid feed material," "solid feedstock," "solid carbonaceous feed material," and "carbonaceous feed material" are used interchangeably and refer to biomass, coal of any rank (including anthracite, bituminous, and lignite), coke produced from coal of any rank, petroleum coke, or bitumen.

As used herein, "biomass" refers to algae or material containing any of cellulose or hemicellulose or lignin, including but not limited to Municipal Solid Waste (MSW), wood (including cut timber; boards, other lumber products, and finished wooden articles, and wood waste including sawdust), and vegetable matter such as grasses and other crops, as well as products derived from vegetable matter such as rice hulls, rice straw, soybean residue, corn stover, and sugarcane bagasse.

As used herein, "light fossil fuel" refers to product useful as fuel that is either found in deposits in the earth and used in the form as found, or produced by reparatory and/or chemical processing of product that is found in deposits in the earth. Examples of light fossil fuel include natural gas, refinery off-gas, naphtha, liquefied petroleum gases, some combination thereof.

As used herein, "product fuel" also referred to as "liquid fuel product" means hydrocarbon material (which includes oxygenated hydrocarbon material) useful as fuel and containing product selected from the group consisting of alkanes liquid at 25° C. and atmospheric pressure, alkanols liquid at 25° C. and atmospheric pressure, and mixtures thereof.

As used herein, "gasifier-syngas" refers to the hydrogen and carbon monoxide containing stream produced in a gasification unit.

As used herein, "$H_2$-rich syngas" refers to the hydrogen and carbon monoxide containing stream produced in a light fossil fuel conversion unit.

As used herein, "gasification unit" includes one or more parallel gasification trains, where a gasification train includes a gasifier employing known gasifier technology as well as high temperature (>200° F.) unit operations associated with a typical gas conditioning unit.

As used herein, "light fossil fuel conversion unit" includes an autothermal reformer (ATR) and/or ATR coupled with a steam methane reformer (SMR).

As used herein, "liquid fuel production unit" refers to the system that produces liquid fuel product from hydrogen and carbon monoxide containing gas. In addition to the catalytic reactors used to synthesize the liquid fuel product, the liquid fuel production unit may include a separation/upgrading/refining section.

As used herein "design production rate" refers to the rate of liquid fuels production when the gasification unit, the light fossil fuel conversion unit, the liquid fuel production unit, as well as any other unit in fluid communication with one or more of these units are all operational and operating at design capacity.

As used herein, "hybrid plant" refers to a plant containing a gasification unit for producing gasifier-syngas from solid feedstock, a light fossil fuel conversion unit for producing $H_2$-rich syngas from light fossil fuels, and a liquid fuel production unit for converting hydrogen and carbon monoxide derived from gasifier-syngas and/or $H_2$-rich syngas into liquid fuel product wherein the light fossil fuel conversion unit provides at least 50% of the hydrogen plus carbon monoxide and less than 80% of the carbon monoxide fed to the liquid fuel production unit when both gasification unit and light fossil fuel conversion unit are operating at their design conditions to produce liquid fuel product at the design production rate.

As used herein "near nameplate capacity" refers to the rate of liquid fuels production in the range of 70% to 110% of the hybrid plant design production rate, where "nameplate capacity" refers to approximately 100% of the hybrid plant design production rate.

As used herein "volumetric gas flow" refers to actual volumetric gas flow at operating temperature and pressure.

In the following description, disclosure of "treatment of a stream", such as disclosure that a stream is reacted or otherwise processed, or that a stream is fed to a processing step or is combined with another stream, is intended to include the indicated treatment of all or less than the entire stream, except where indicated otherwise herein.

Figure 1:
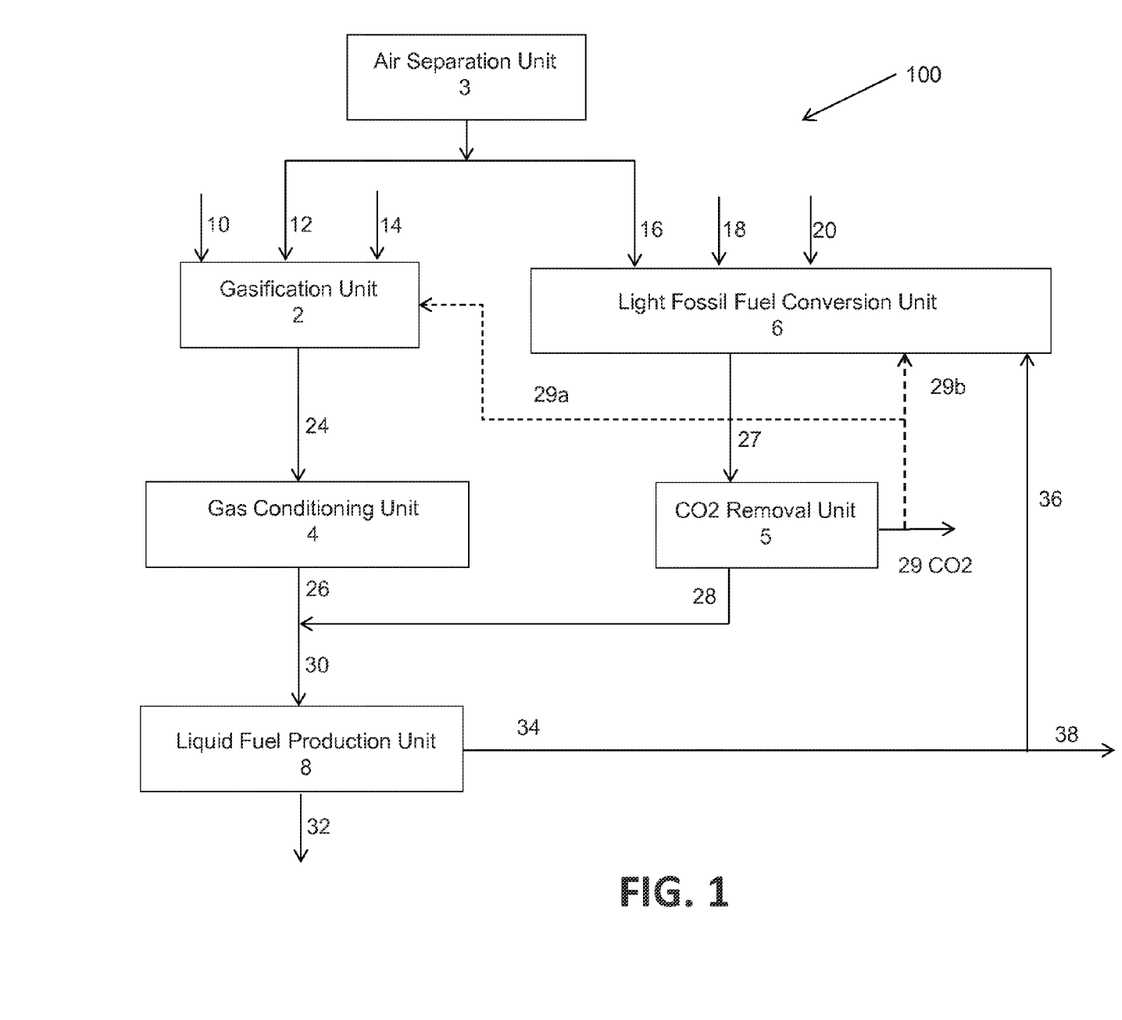
FIG. 1 is a block diagram of the hybrid plant.

With reference to FIG. 1, hybrid plant 100 includes a gasification unit 2, a gas conditioning unit 4, a light fossil fuel conversion unit 6, a liquid fuel production unit 8, an optional carbon dioxide ($CO_2$) removal unit 5, and an air separation unit 3 (optionally an offsite supply by pipeline). Solid carbonaceous feed material 10 is reacted with oxygen 12 and steam 14 in the gasification unit to produce a gaseous stream 24 which contains at least hydrogen and carbon monoxide and which typically also contains other substances such as carbon dioxide, water vapor, hydrocarbons (including methane), particulate matter, and sulfur and nitrogen containing species. The sulfur and nitrogen containing species, volatilized tars (if any), particulate matter and at least a portion of carbon dioxide present in stream 24 is removed in gas conditioning unit 4 to form gasifier-syngas stream 26. Light fossil fuel 18, steam 20 and oxygen 16 are processed in light fossil fuel conversion unit 6 to form synthesis gas stream 27. A portion of the $CO_2$ is removed from synthesis gas 27 in $CO_2$ removal unit 5 as stream 29. All or part of the $CO_2$-rich stream 29 can be used elsewhere in the process, e.g. gasification unit 2 (stream 29a), light fossil fuel conversion unit 6 (stream 29b), or upgraded for external use or sequestration. Gasifier-syngas stream 26 and $H_2$-rich syngas stream 28 are mixed to form stream 30, and converted in liquid production unit 8 to form liquid fuel product 32. Optionally, portions or all of steams 26 and 28 can be fed to unit 8 separately. The Air separation unit 3 generally, is an on-site cryogenic distillation unit that produces oxygen at high pressure and greater than 98 mole % purity for use in the gasification unit and the fossil fuel conversion unit. Optionally, oxygen can be supplied from an adsorption based unit or from a pipeline in fluid communication with one or more cryogenic air separation units.

Gasification unit 2 may comprise one gasifier or a plurality of gasifiers connected in parallel. Gasifiers for different types of carbonaceous feed materials, e.g. coal, petcoke, biomass, are well known in the art. A hydrogen and carbon monoxide containing stream 24 is generated by breakdown of the solid carbonaceous feed material 10 under conditions such that there is not a complete oxidation to water and carbon dioxide. The stream 24 produced from gasification of solid carbonaceous feed material typically contains hydrogen and carbon monoxide at a molar ratio less than 1.5:1 and generally less than 1:1.

As stream 24 typically includes impurities that need to be removed prior to feeding stream 26 to liquid production unit 8 as described below, stream 24 is preferably treated in gas conditioning unit 4 to remove impurities. Depending on the feedstock, type of gasifier and gasifier operating conditions the impurities may include particulates, tars, acid gases such as $CO_2$, ammonia, sulfur containing species, and other inorganic substances such as alkali compounds. Impurities may be removed in one unit operation or in a series of unit operations to remove specific contaminants. Gas conditioning unit 4 employs known technologies such as: scrubbers, cyclones and filters to remove particulates; COS hydrolysis units for conversion of COS to $H_2S$; acid gas removal technologies to remove sulfur compounds and/or $CO_2$; adsorbent beds for reducing impurities to very low levels. The gas conditioning unit 4 also includes any required cooling to ready the gasifier syngas for treatment in the acid gas removal or other conditioning units. Generally, steam is produced in a portion of the gas cooling section for use in other parts of the process. Details are not shown, but should be obvious to those skilled in the art. Use of a high temperature gasifier, e.g. entrained flow gasifier, where the gasifier-syngas exits the gasification section of the gasifier at >1500° F. and generally >1800° F. (note: temperatures leaving quench and/or heat recovery sections can be much lower than 1500° F.), reduces the complexity of gas conditioning unit 4. In particular, tar and methane content of gasifier-syngas from a high temperature gasifier tends to be quite low to non-existent. In this situation, the gas conditioning unit 4 may primarily entail cooling/heat recovery, COS hydrolysis, acid gas removal and adsorbent beds for polishing removal of sulfur and other contaminants to levels acceptable for liquid synthesis catalysts. For the case of multiple gasification trains, each train will include a gasifier as well as high temperature (>200° F.) unit operations associated with the gas conditioning section. This includes scrubbers, cyclones and filters to remove particulates; COS hydrolysis units for conversion of COS to $H_2S$ as well as the heat recovery section. It is typical to have a common acid gas removal system for sulfur and $CO_2$ removal as well as adsorbent beds for polishing removal of sulfur and other contaminants to levels acceptable for liquid synthesis catalysts.

The resulting conditioned gaseous stream 26 from gas conditioning unit 4 contains at least hydrogen and carbon monoxide in a molar ratio of hydrogen to carbon monoxide considerably less than two. The exact composition can vary widely depending on the solid carbonaceous feed material, gasifier type and gasifier operating conditions. Generally the molar ratio of hydrogen to carbon monoxide is less than about 0.6 in gasifier-syngas from coal or petcoke, and less than 1.2 in gasifier-syngas from biomass. Before stream 26 is fed to liquid fuel production unit 8, it is combined with stream 28 that contains hydrogen and carbon monoxide formed in light fossil fuel conversion unit 6.

Air separation unit 3 typically is an on-site cryogenic distillation unit that supplies oxygen to the gasification unit 2. Ambient air is compressed, purified to remove impurities, cooled, and distilled at cryogenic temperatures using known technologies. Liquid oxygen is withdrawn from distillation column, pumped to elevated pressure, vaporized and superheated. The air separation unit 3 may contain one or more trains of equipment such as for feed air compression, purification, heat exchange, cryogenic distillation, liquid oxygen pumping, etc. The air separation unit can be designed to supply high pressure high purity oxygen to both gasification unit and light fossil fuel conversion unit. Oxygen may be provided at a single high pressure or different pressures to satisfy gasification unit 3 and light fossil fuel conversion unit 6 requirements.

Figure 2:
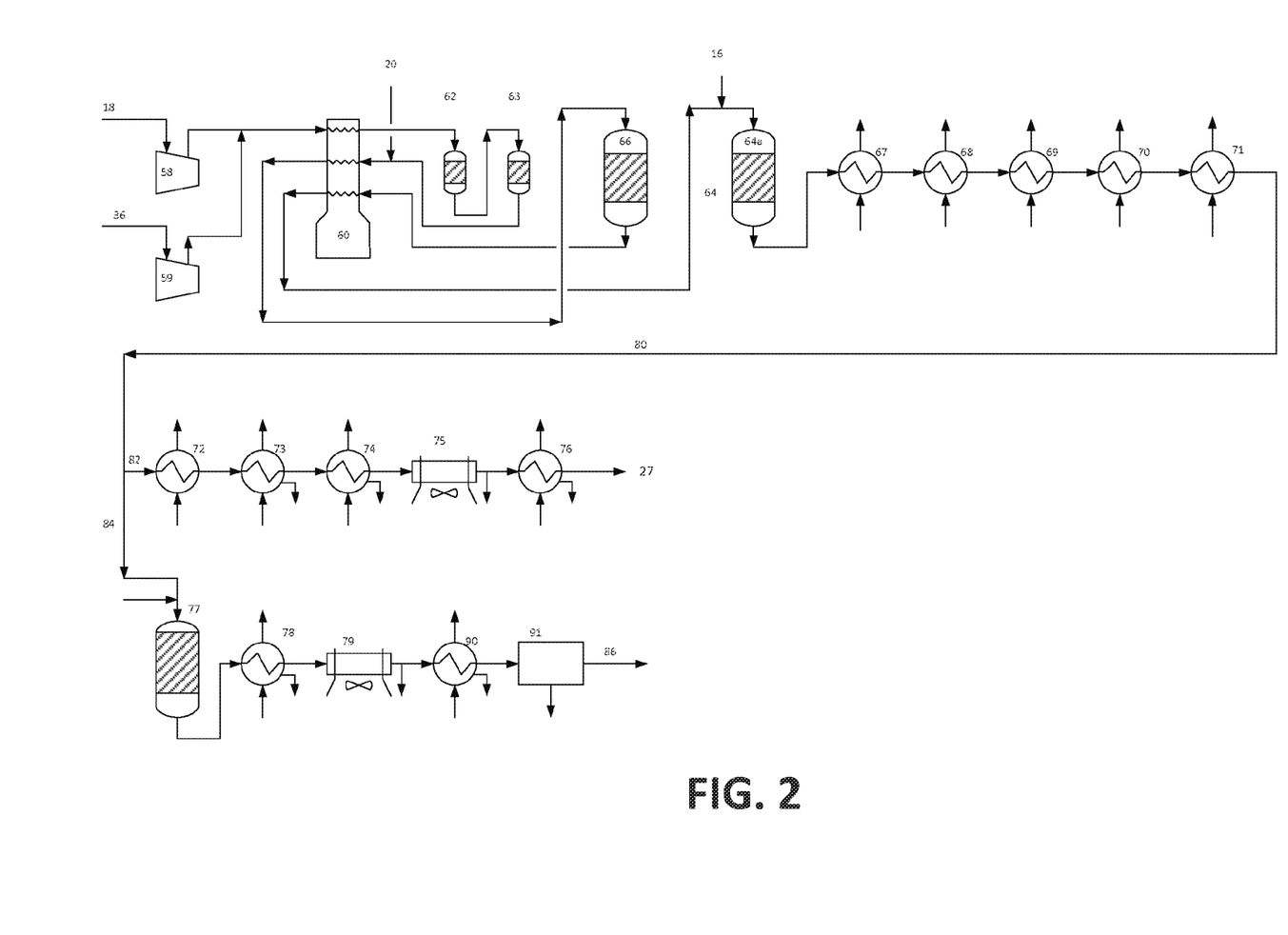
FIG. 2 is a flow diagram of a light fossil fuel conversion unit containing autothermal reformer (ATR)
Figure 3:
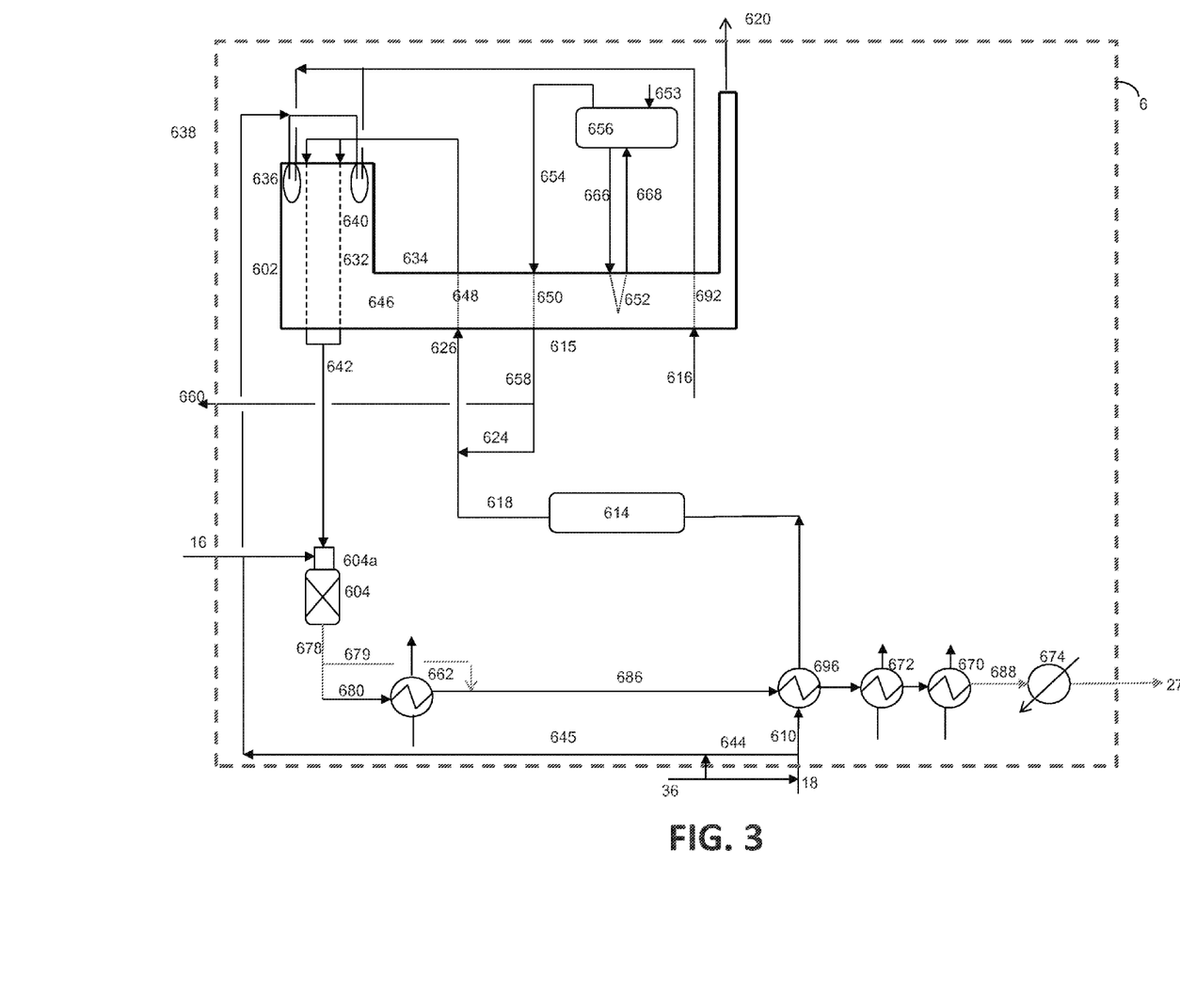
FIG. 3 is a flow diagram of an alternate light fossil fuel conversion unit containing a steam methane reformer (SMR) coupled to a downstream autothermal reformer.

Light fossil fuel conversion unit 6 processes light fossil fuel 18, steam 20, oxygen 16 to produce hydrogen and carbon monoxide containing gas stream 27. By-product fuel gas 36 may also be an input to the light fossil fuel conversion unit. Options for the light fossil fuel conversion unit include, autothermal reformer (ATR), or a combination such as a SMR coupled to a downstream ATR (also known as an SMR with secondary reformer). FIG. 2 shows a preferred configuration employing an ATR, and FIG. 3 shows another preferred configuration employing a SMR coupled to a downstream ATR. Stream 27 typically contains hydrogen, carbon monoxide, carbon dioxide, water vapor, methane and inerts such as nitrogen, argon. The composition of stream 27, and in particular the ratio of hydrogen to carbon monoxide, primarily depends on the type of fossil fuel conversion unit, ratio of steam to carbon fed to unit 6, gas temperature leaving the light fossil fuel conversion reactor and the amount of $CO_2$ being fed to unit 6. A portion of the carbon dioxide in stream 27 can be optionally removed in unit 5. The carbon dioxide removal process can be carried out using commercially available technologies such as those employing a physical solvent (e.g. methanol) or a chemical solvent (alkanolamine), or which employ physical adsorbent technology such as a PSA or VPSA. When the gasifier is operational, a portion or all of $CO_2$-rich stream 29 may be sent to the gasification unit 2. All or a portion of the $CO_2$-rich stream may also be used within the light fossil fuel conversion unit 6.

Stream 28 typically has hydrogen to carbon monoxide ratio of greater than about 1.8:1. The exact ratio is adjusted based on the type of liquid fuel being synthesized in liquid fuel production unit 8 as well as the operating status of the gasifier, e.g. operating at design conditions or partially operating or shut down. Stream 28 is combined with stream 26 to form stream 30 that contains hydrogen and carbon monoxide in a molar ratio of at least 1.6:1. Stream 30 fed to a liquid fuel production unit 8 producing Fischer-Tropsch liquids contains hydrogen and carbon monoxide in a ratio that is generally in the range of 1.6:1 to 2.2:1. Stream 30 fed to a liquid fuel production unit 8 producing methanol contains hydrogen, carbon monoxide and carbon dioxide such that the $(H_2-CO_2)/(CO+CO_2)$ ratio is in the range of 2 to 2.4. Depending on the ratio of CO to $CO_2$, the $H_2/CO$ ratio is typically in the range of 2.2 to 3.6.

When the gasification unit 2 is operating at design capacity, the light fossil fuel conversion unit 6 is operated such that hydrogen to carbon monoxide ratio of stream 28 is greater than 2.2:1. For feeding to a liquid fuel production unit producing FT liquids, the hydrogen to carbon monoxide ratio is preferably in the range of 2.2:1 to 4:1, and for feeding to a liquid fuel production unit producing methanol, the hydrogen to carbon monoxide ratio is preferably in the range of 3.5:1 to 5:1.

When the gasification unit is not operational, the light fossil fuel conversion unit 6 operating conditions are adjusted such that hydrogen to carbon monoxide ratio of stream 28 for producing FT liquids is in the range of 1.6:1 to 2.2:1 or for producing methanol is in the range of 2.2:1 to 3.6:1.

When the gasification unit is operating at part capacity, the operating conditions in the light fossil fuel conversion unit 6 are adjusted such that hydrogen to carbon monoxide ratio of stream 28 is in the range between those described above.

With reference to FIG. 2, the light fossil fuel conversion unit 6 contains an autothermal reformer 64 that has a first reaction zone formed by a burner (not shown). Exothermic oxidation reaction releases heat that gets consumed in subsequent endothermic reforming reactions. An example of exothermic reaction that occurs in the first reaction zone is:

The resultant intermediate product from the first reaction zone then passes to a catalyst bed below the burner reforming and water gas shift reactions take place. The overall reactions are typically defined by the following:

$$CH_4 + H_2O \Leftrightarrow CO + 3H_2$$

$$CO_2 + H_2 \Leftrightarrow CO + H_2O$$

$$CH_4 + CO_2 \Leftrightarrow 2CO + 2H_2$$

The exothermic oxidation reactions provide the energy necessary to drive steam reforming reactions over the catalyst in the autothermal reformer. No external heating is provided. Any supported catalyst active for steam reforming may be used. For instance, Group VIII metals (i.e. Fe, Co, Ni, Ru, Rh, Pd, Os, Ir, Pt) may be loaded onto ceramic or metal-based supports, such as pellets, shaped particles, honeycomb monoliths, foam monoliths, or corrugated foil monoliths. A bed of Ni-loaded ceramic shaped particles could be used. The catalyst bed could include a metal, corrugated foil monolith as a support for one or more noble metal catalysts (e.g. Pt, Pd, Rh, Ru).

Natural gas 18, containing a small amount of hydrogen from stream 86 or from hydrogen-containing byproduct gas stream 36, is heated in a fired heater 60 prior to desulfurization in hydrotreater 62 and sulfur guard bed 63, which typically contains adsorbents like ZnO and/or CuO. Superheated steam is added as stream 20 to the desulfurized process gas stream, which is then further heated in the fired heater to temperatures up to about 1000° F. prior to entering a pre-reformer 66. If hydrogen-containing byproduct gas stream 36 from liquid fuel production unit 8 is also supplied as feed to the light fossil fuel conversion unit 6 then stream 36 is also preheated in the fired heater 60 prior to introducing in the pre-reformer 66. The pre-reformer is an adiabatic catalyst filled reactor that reforms and converts heavy hydrocarbons (C2+) to methane, hydrogen and CO. In addition, a small amount of methane is also reformed. As a result of reforming, the temperature leaving the pre-reformer is generally lower than the feed temperature. The partially reformed gas is reheated to temperatures up to about 1100° F. prior to entering the autothermal reformer 64. All or a portion of $CO_2$ stream 29 from the $CO_2$ removal unit 5 shown in FIG. 1 can be added directly to the heated partially reformed gas prior to entering the fired heater 60, or entering the pre-reformer 66 or added with the oxygen stream 16 entering the ATR.

When the gasification unit is operating at reduced capacity or is not operational then less than design quantity of oxygen is needed in the gasification unit. The oxygen from air separation plant that would have been fed to the gasification unit becomes available. At least some of this available oxygen can be routed to light fossil fuel conversion unit to increase oxygen feed to ATR. To maintain liquid fuel production at a desired rate, flow of light fossil fuel feed to the ATR is increased to produce more $H_2$-rich syngas and compensate for reduced gasifier-syngas flow available from the gasification unit. The ATR is also operated differently under this scenario.

The light fossil fuel conversion unit 6 is designed for flow rates of steam 20 that correspond to a steam to carbon ratio (S/C) generally in the range of about 1 to 3. The preferred design value of steam to carbon ratio when the hydrogen and carbon monoxide containing gas from the light fossil fuel conversion unit is used to make FT liquids is in the range of about 1 to 2, and when methanol is the desired liquid fuel product then the preferred design value of steam to carbon ratio is in the range of about 2 to 3. Under certain conditions such as when the gasification unit 2 is operating at reduced capacity or is not operational, the flow rate of steam 20 can be adjusted to lower the S/C ratio approaching a design value of about 0.4 to allow for production of $H_2$-rich syngas stream 28 having a $H_2$:CO ratio near that required by the liquids synthesis technology (1.6:1-2.2:1 for FT liquids and 2.2:1-3.6:1 for methanol).

The ATR is designed for temperature of gas leaving ATR to be about 1700° F. (+/−150° F.) when the hybrid plant is operating at design conditions. When the gasification unit is unavailable, then the ATR exit temperature is allowed to approach the upper limit of ATR operations 1900° F. Depending on the liquid fuel product type, all or a portion of the $CO_2$ stream 29 is returned to the ATR when the gasification unit is not operating or operating below design capacity.

Heat can be recovered from the gas leaving the ATR in various ways. FIG. 2 provides one illustration. Hot syngas from the ATR is sent to a first process gas boiler 67, which generates wet steam at pressures in excess of 1100 psia. Syngas exiting the high pressure boiler is then sent to a high pressure steam superheater 68, which increases the temperature of high pressure steam from the saturation temperature of ~550° F. to 1000° F. The syngas is sent to a second steam superheater 69 to superheat medium pressure (~750 psig) saturated steam to about 680° F. The syngas then enters a third superheater 70, which increases the temperature of ~185 psig saturated steam to about 560° F. The syngas is subsequently sent to a second process gas boiler 71 where wet steam at around 750 psig is produced. Though not shown, wet steam leaving each of the boilers is sent to a corresponding steam drum where saturated steam is separated from the water and superheated in the aforementioned superheaters. The water for the steam drums is provided by boiler feed water (BFW) streams preheated in various BFW heaters. For the case discussed in FIG. 2, a portion of the high pressure superheated steam is available for power generation. A portion or all of superheated steam at 750 psig is used as stream 20 to adjust the S/C ratio in the ATR. The low pressure (~185 psig) superheated steam is available for other uses within the hybrid plant. Steam can be exported to other users if an appropriate user is within a reasonable distance of the hybrid plant.

Typically, greater than 80% of stream 80 exiting the second process gas boiler 71, is sent as stream 82 to a boiler feed water (BFW) heaters 72 and 73 to preheat BFW and then to heat demineralized water, which is subsequently sent to a deaerator (not shown in FIG. 2). Syngas exiting the demin water heater 74 is sent to a phase separator (not shown in FIG. 2) to remove condensate and then further cooled with air cooled and/or water cooled heat exchangers 75 and 76. This is followed by condensate removal in a phase separator, which is not explicitly shown in FIG. 2. Syngas stream 27 leaving the condensate removal step is sent to $CO_2$ removal unit 5 (see FIG. 1).

Depending on the liquid fuel product, the hybrid plant and in particular the liquid fuel production unit 8 may require $H_2$. For example, if FT liquids are being synthesized, $H_2$ is required in the refining/upgrading step and possibly in the FT synthesis step. Accordingly, a portion of stream 80, typically less than 20%, is sent as stream 84 to a shift reactor 77. Some superheated steam may be added prior to the shift reactor. Due to the exothermic nature of the water gas shift reaction, temperature of the syngas leaving the shift reactor is typically at around 800° F. versus around 600° F. at the inlet. The syngas is sent to another BFW heater 78. This is followed by condensate removal (phase separator not explicitly shown in FIG. 2), cooling in air-cooled and/or water-cooled heat exchangers 79 and 90 and another condensate removal step (phase separator not shown in FIG. 2). The syngas is sent to a PSA unit 91, which produces $H_2$ stream 86. This can be used within the hybrid plant or exported. Preferably, most of the $H_2$ thus produced is used within the hybrid plant. PSA tail gas can be used as a fuel in the fired heater 60. Other fuels such natural gas or mixtures of by-product gases from the liquid fuel production unit can be used as needed to provide the energy needed for heating the various streams in the fired heater. The fired heater can also provide heat for boiler feed water heating and for demineralized water heating prior to de-aerating.

FIG. 3 is another configuration of a light fossil fuel conversion unit 6 that couples a steam methane reformer 602 to a downstream autothermal reformer 604. Natural gas 18 is converted in the light fossil fuel conversion unit 6 to produce hydrogen and carbon monoxide containing synthesis gas 27. Natural gas is shown simply for purposes of illustration in that light fossil fuel conversion unit 6 could be designed to process any other type of hydrocarbon containing stream such as naphtha or refinery offgases or some combination thereof. Natural gas 18 is divided into SMR feed stream 610 and SMR fuel stream 644. The SMR feed stream 610 after a small quantity of hydrogen addition contained in stream 36 or some other source is heated and desulfurized in desulfurization unit 614 using known technologies such as hydrotreatment and sulfur guard bed (for e.g. zinc oxide bed) to remove any sulfur containing species present. Optionally all of stream 36 may be processed with natural gas feed stream 18 to form stream 610, or a portion processed with natural gas feed stream 18 to form stream 610 and remaining with natural gas fuel stream 644 to form stream 645. The desulfurized feed gas stream 618 is combined with a first superheated steam stream 624 to form a reactant stream 626 that is heated in 648 and then introduced into the reactor tubes 640 of steam methane reformer 602. Optionally stream 626 that is heated in 648 could be sent to a pre-reformer with subsequent reheating in convection section 634 prior to entering unit 602 (not shown.).

Steam methane reformer (SMR) 602 includes a reactor section 632 and a convective section 634. As illustrated, burners 636 fire into reactor section 632 to heat reactor tubes 640 containing reforming catalyst. Although only two burners and two reactor tubes are shown in the illustration, as would be known to those skilled in the art, there would be multiple burners and many reactor tubes in a steam methane reformer. The fuel for the burners 636 is provided by the natural gas stream 644 and often by at least a portion of byproduct stream 36 produced in the liquid production unit 8. Catalyst packed reactor tubes 640 located in the reactor section of the steam methane reformer are fed with reactant stream 626 after having been heated in 648. Steam methane reforming reactions, and water-gas shift reactions occur within reactor tubes 640.

The overall reactions are typically defined by the following:

Steam methane reforming reactions are endothermic and hence, heat is supplied to the catalyst packed reactor tubes to support the reactions by burners firing into the reactor (radiant) section of the steam methane reformer. The energy input needed to carry out endothermic reactions is provided by combusting fuel stream with air, oxygen, or oxygen-enriched air stream 616. Combustion creates flue gas stream 646 leaving the radiant section 632. Heat is recovered in convective section 634, using heat exchangers 648 (to heat stream 626), 650 (to superheat steam) and 652 (to generate steam), and 692 (to preheat stream 616).

Conversion of the light fossil fuel stream 18 (e.g. natural gas, methane, naphtha, liquefied petroleum gases), with steam 624, in SMR 602 results in gaseous product stream 642 containing hydrogen and carbon monoxide in a molar ratio ($H_2$:CO) considerably greater than 2:1 and typically greater than 4:1. The ratio of hydrogen to carbon monoxide in stream 642 depends on the ratio of steam to carbon in stream 626 and temperature of stream 642 at SMR exit. Increasing the ratio of steam to carbon fed to SMR 602 increases the ratio of hydrogen to carbon monoxide in stream 642, but also can increase the overall energy requirements of the system (taking into account the incremental additional energy required to produce additional steam that is fed to SMR). Typically SMR product gas (stream 642) leaves the SMR at a temperature of about 1600 F.

With reference to FIG. 3, stream 642 from SMR 602 that contains hydrogen, carbon monoxide, carbon dioxide, methane and water vapor is fed to the burner section 604a of autothermal reformer 604. The ATR is designed to achieve a reduction in methane content of syngas stream 642 by adding oxygen 16 to provide the heat to raise the temperature of the syngas and further processing the syngas under adiabatic conditions. Although not illustrated, steam and/or $CO_2$ may be added to the oxygen stream 16 and/or the oxygen stream 16 could be preheated prior to being introduced into autothermal reformer 604. Also not shown is a portion or all of stream 36 that is mixed with stream 18 could be added to stream 642 preferable after preheating in unit 634.

ATR (secondary reformer) coupled to an SMR is designed to produce additional hydrogen and carbon monoxide. Combustible gases in the SMR product gas react with oxygen, generating heat for facilitating reforming reactions over a catalyst bed in the ATR in an adiabatic manner. The resulting ATR product gas 678 exits the autothermal reformer 604 at a temperature of about 1700° F. to about 1900° F. Typically gas 642 entering the ATR will have methane concentrations that range from about 4 mole % (on a dry basis) when exiting SMR 602 at a high temperature, for example about 1600° F. to as much as 14 mole % (on a dry basis) when exiting at a lower temperature, for example 1400° F. The gas 678 exiting the ATR will have methane concentrations typically less than about 1 mole % (on a dry basis). Lower SMR exit temperatures require more oxygen to achieve the normal ATR exit temperatures due to heat that must be generated to provide the sensible heat to raise the temperature of gas stream 642 and, more importantly, to provide the heat to drive the reforming of the higher methane content in stream 642. The $H_2$:CO ratio drops somewhat as the quantity of oxygen increases.

Gas 678 exiting the ATR is generally fed to process gas boiler 662 for cooling. It is not unusual for a bypass to be included in the design of process gas boiler 662 for better temperature control. The resulting cooled synthesis gas stream 686 is used to preheat the light fossil fuel stream 610 in heat exchanger 696 and then further cooled in boiler feed water heater 672, demineralized water heater 670, and cooler 674 to form synthesis gas 27. As would be apparent to those skilled in the art, alternate heat exchange arrangements are possible for recovering heat in hydrogen and carbon monoxide containing gas stream 678.

A steam generation system is integrated into the light fossil fuel conversion unit 6 and contains elements known in the art to provide at least some of the steam needed for steam methane reforming reactions. For example heat exchangers 652 and 650 provided within the convective section 634 generate and superheat steam. A steam stream 654 from a steam drum 656 is superheated within heat exchanger 650 to produce a superheated steam stream 658. Depending on superheated steam production rate, stream 658 may be divided into a first superheated steam stream 624 and an export steam stream 660. Although not illustrated, the steam generated by a process gas boiler 662 is also superheated within convective section 634 and then used as part of the makeup of first superheated steam stream 624 and export steam stream 660. Saturated steam 654 is separated within steam drum 656 from steam containing stream 668 that is fed to steam drum 656 from boiler 652. Saturated boiler feed water is fed to boiler 652 as stream 666. Steam drum 656 is fed with water 653 heated in boiler feed water heater 672 and demineralized water heater 670 provides hot water for deaeration (not shown) through indirect heat exchange with hydrogen and carbon monoxide containing gas stream 686. Although not illustrated, boiler feed water heater 670 is fed water pumped from the deaerator.

Low grade heat remaining in gas 688 after having passed through heat exchange equipment 662, 696, 672 and 670 is recovered and/or rejected to atmosphere using cooler 674 which could be a combination of air cooling and water cooling.

During normal operation (i.e. gasifier operating at design capacity) a minimal amount of oxygen 16 is added to the ATR 604 and the temperature of stream 678 can range from that for SMR's, greater than about 1550° F. to the upper region of a secondary reformer (ATR), less than about 1800° F. Resulting $H_2$ to CO ratio in stream 27 is greater than 3:1 and typically greater than 4:1.

When the gasifier is not operational or operating at less than design capacity, the firing rate of the SMR (determined by the flows of stream 644 and 616) is held constant. Consequently, the heat exchange performance of the radiant and convective sections of the SMR 602 remains unchanged. The flow of light fossil fuel 610 to the reactor section 632 is increased. The amount of steam being added through stream 624 is adjusted to achieve the desired S/C ratio of the gas 626 entering the reactor section 632 of the SMR. The desired S/C ratio under this condition is usually less than the S/C ratio when gasifier is operating at design capacity. Consequently, the temperature of stream 642 drops when compared to the normal operating case. A portion of available oxygen 14, typically used in gasification unit 2, is diverted to ATR 604 to raise the temperature of stream 678 to at least 1550° F. and possibly to as much as 1900° F. The preferred temperature will generally be in the range of 1700° F. to 1900° F. Heat exchange equipment such as 662 and those downstream of 662 will be designed to manage the variable heat duties that result from increasing the flow of light fossil fuel 18. Under this scenario, it is possible to achieve a $H_2$/CO ratio of less than 3.5:1 and preferably less than 3.2:1 in stream 27. To achieve $H_2$/CO ratios close to that required for liquid fuels production when gasification unit syngas capacity is reduced, all or a portion of the $CO_2$-rich stream 29 recovered from unit 5 is returned to the light fossil fuel conversion unit 6 to further reduce the $H_2$/CO ratio of stream 27. All or part of stream 29 can be added to streams 18, 618, and/or 16. Returning $CO_2$ will further reduce the $H_2$/CO ratio of stream 27 to less than 3:1 and possibly less than 2.6:1. If the $CO_2$-rich stream is added through stream 16 to the ATR, the light fossil fuel feed heater 696, desulfurization unit 614 and heat exchanger 648 do not need to be oversized for the scenario when gasifier is operating at or below design capacity.

FIGS. 2 and 3 show two configurations of light fossil fuel conversion unit 6, it is possible to practice variations that are not illustrated. For example the light fossil fuel conversion unit may contain:

an SMR and an ATR operating in parallel, each converting light fossil fuel into hydrogen and carbon monoxide containing streams that may be combined for liquid fuels production
  SMR and ATR such that light fossil fuel feed is divided in two portions, a first portion fed to SMR and a second portion fed to ATR separately or mixed with SMR product gas.

The supply of oxygen to gasification unit 2 and light fossil fuel conversion unit 6 can be from same or different source. Although not illustrated, steam may be added to the oxygen stream 16 and/or the oxygen stream 16 could be preheated prior to being introduced into the autothermal reformer.

With reference to FIG. 1, stream 26 and stream 28 serve as feed to the liquid fuel production unit 8. These streams can be fed separately or as a mixed stream 30. Depending on the operating pressure of liquid fuel production unit 8 streams 26, 28 or 30 may need to be compressed or depressurized (through a valve or an expander). The liquid fuel production unit employs a catalytic conversion process, (e.g. methanol synthesis, Fischer-Tropsch process) to produce liquid fuel product. Higher pressure gasifiers such as entrained flow technologies can result in stream 30 pressures sufficient for use in unit 8 without compression. If the end-product is a diesel-type of fuel, a single stage of compression may suffice, and in some cases no compression may be required. For alcohols, (e.g. methanol, ethanol), 2-3 stages of compression may be required. Obviously compressing the blended stream 30 provides the benefit of a reduction in the amount of equipment needed for compression versus separately compressing streams 26 and 28 to the desired pressure.

Considering Fischer-Tropsch conversion in general, the Fischer-Tropsch reaction may be carried out in any reactor that can tolerate the temperatures and pressures employed. The pressure in the reactor is typically between 300 psia and 1500 psia, while the temperature may be between 400° F. and 700° F. Preferably, the Fischer-Tropsch hydrocarbon synthesis stage is a low temperature Fischer-Tropsch hydrocarbon synthesis stage. The operating pressure of the reactor(s) will typically be between 300 psia and 700 psia. The reactor will thus contain a Fischer-Tropsch catalyst, which could be in particulate form. The catalyst may contain, as its active catalyst component, Co, Fe, Ni, Ru, Re and/or Rh. The catalyst may be promoted with one or more promoters selected from an alkali metal, V, Cr, Pt, Pd, La, Re, Rh, Ru, Th, Mn, Cu, Mg, K, Na, Ca, Ba, Zn and Zr. The catalyst may be a supported catalyst, in which case the active catalyst component, e.g. Co, is supported on a suitable support such as alumina, titania, silica, zinc oxide, or a combination of any of these. The preferred embodiment in this invention uses a Co-based catalyst. For a biomass feedstock, the preferred reactor configuration is a fixed bed tubular reactor with the Co-based catalyst packed in tubes. For coal, the preferred reactor configuration is a slurry bed reactor where the Co-based catalyst is in particulate form. Fixed bed tubular reactors, while less preferable, could also be deployed.

In the Fischer-Tropsch conversion, the hydrogen and carbon monoxide in stream 30 react under pressure in the presence of a catalyst at reaction temperature in the indicated range to yield a mixture of alkanols, alkanes, or both, which may contain 1 to greater than 60 carbon atoms. Water and carbon dioxide are also produced.

As the Fischer-Tropsch reaction is exothermic, steam-producing cooling coils are preferably present in the Fischer-Tropsch reactors to remove the heat of reaction. This steam can be fed to light fossil fuel conversion unit 6 as part of the steam reactant in the steam methane reforming reaction or used elsewhere in the overall process, e.g. regeneration of amine solvent, drying of solid feedstock. Fresh catalyst is preferably added to the FT reactor within liquid fuel production unit 8 when required without disrupting the process to keep the conversion of the reactants high and to ensure that the particle size distribution of the catalyst particles is kept substantially constant.

The manner of carrying out a variation of the Fischer-Tropsch reaction for producing alcohols from syngas is well known and has been practiced for several years. Useful disclosure is found in "Synthesis of Alcohols by Hydrogenation of Carbon Monoxide". R. B. Anderson, J. Feldman and H. H. Storch, Industrial & Engineering Chemistry, Vol. 44, No. 10, pp 2418-2424 (1952). Several patents also describe different aspects of the Fischer-Tropsch conversion process that can be practiced to produce alkanols including ethanol. For example, U.S. Pat. No. 4,675,344 provides details on process conditions, (e.g. temperature, pressure, space velocity, as well as catalyst composition) to optimize the Fischer-Tropsch process for increased production of $C_2$ to $C_5$ alcohols versus methanol. This patent also indicates that desirable hydrogen: carbon monoxide ratio in the gas feed stream is in the range of 0.7:1 to 3:1.

When the desired product fuel is methanol, the liquid fuel production unit 8 is designed and operated in a known manner to favor the formation of methanol. Hydrogen and carbon oxides react over a catalyst such as copper-zinc catalyst at elevated pressure to form methanol.

$$2H_2+CO \Longleftrightarrow CH_3OH$$

$$3H_2+CO_2 \Longleftrightarrow CH_3OH+H_2O$$

Methanol thus produced could subsequently be converted into gasoline using ExxonMobil's MTG or methanol to gasoline process. This process will generate an LPG by-product stream that could be sent to the light fossil fuel conversion unit 6.

The hybrid plant can also be designed to produce additional products, for example hydrogen, carbon monoxide, and/or mixture containing both. The gasification unit 2, gas conditioning unit 4, and light fossil fuel conversion unit 6 can be sized accordingly to produce hydrogen and carbon monoxide containing streams in sufficient quantities to satisfy liquid fuel production and additional products production goals.

For example when high purity hydrogen is to be produced as additional product, then one or more of the hydrogen and carbon monoxide containing streams produced in the light fossil fuel conversion unit 6 can be subjected to water gas shift reactions in a high or medium temperature water gas shift reactor(s) or a combination of high temperature and low temperature shift unit. The water gas shift reactor configuration, catalyst and operating conditions are selected based on feed gas composition (steam to CO ratio), whether sulfur containing species are present, which depends on location in the flow sheet from where the hydrogen and carbon monoxide containing stream is sourced. Water gas shift reactor product gas after appropriate cooling is fed to a pressure swing adsorption (PSA) unit to recover high purity hydrogen, for e.g. purity greater than 99 mole % hydrogen on a dry basis.

When the liquid fuel product is methanol, high purity hydrogen can also be recovered from the liquid fuel production unit 8 purge stream (not shown). The purge stream can be fed to a PSA for this purpose. Alternately a polymeric membrane unit can be used to produce a hydrogen enriched stream which as needed is further processed in a PSA to produce hydrogen. The hydrogen can be recycled to the feed of the methanol production unit or exported for other uses. In most cases, membrane separation units will require compression of the hydrogen stream prior to further processing or use. The hydrogen that is exported can be used in other industrial or refining operations.

It should be recognized that an object of this invention is to maintain liquid fuel production unit 8 near the design capacity by producing sufficient $H_2$-rich syngas from the light fossil fuel conversion unit 6 even when the gasification unit 2 is not producing any gasifier-syngas or producing gasifier-syngas at reduced capacity.

To maintain liquid output near design capacity it is necessary to produce more synthesis gas in the light fossil fuel conversion unit to make-up for the reduction in gasifier-syngas flow from the gasification unit. The adjustments in the light fossil fuel conversion unit to achieve the increased CO plus hydrogen flow include light fossil fuel feed flow, oxygen flow to ATR, steam input (steam to carbon ratio), $CO_2$ recycle to feed, operating temperature of ATR (FIG. 2), operating temperatures of SMR and/or ATR (FIG. 3). The choice and degree of adjustment of one or more of these depends on the operational status of the gasification unit, whether prior to adjustment the gasification unit was operational at design capacity or at reduced capacity or not operational.

Three hybrid plant configurations have been simulated for illustration purposes, results are described below.

Example 1

Methanol Production Hybrid Plant

The hybrid plant and light fossil fuel conversion unit configurations illustrated in FIGS. 1 and 2 are simulated as a world scale methanol facility containing a gasification unit 2, gas conditioning unit 4, light fossil fuel conversion unit 6 containing an ATR, optional $CO_2$ removal unit 5 for removing $CO_2$ from synthesis gas 27, and a liquid fuel production unit 8. Three operating modes are simulated. In case 1 the hybrid plant is operational at design conditions producing methanol at a design production rate of nominal 5004 tonnes/d. In case 2, gasification unit is not on stream, and in case 3, the gasification unit is operating at 50% capacity. Case 3 is equivalent to a system with two gasification trains with only one gasification train operational. Table 1 summarizes simulation results. At design conditions (case 1) the gasification unit 2 consumes 1400 tons/d of oxygen to gasify 1590 tons/d of Pittsburgh #8 coal and produces 101.3 MMSCFD of gasifier-syngas having a hydrogen to carbon monoxide ratio of 0.5. The ATR system in the light fossil fuel conversion unit 6 consumes 2546 tons/d oxygen and operates at a steam to carbon ratio of 2.8 and exit temperature of 1650° F. to provide $H_2$-rich syngas stream 28 having a hydrogen to carbon monoxide ratio of 4.4. The light fossil fuel conversion unit 6 provides 72% of hydrogen plus carbon monoxide and 47% of carbon monoxide in the feed to the liquid production unit 8. In case 2 gasifier-syngas 26 available from the gasification unit 2 is nil and in case 3 it is 50% of design capacity, however in case 2 and case 3 the methanol production rate is maintained at design value by:
  increasing light fossil fuel feed to ATR system
  increasing oxygen feed to ATR system by diverting a portion of available oxygen that would have been fed to the gasification unit (approximately 61% in case 2 and 32% in case 3);
  decreasing steam to carbon ratio to 0.6 in case 2 and to 1.4 in case 3.

In this example, $CO_2$ is not recycled to the ATR. The flow rate of gas leaving ATR in actual cubic feet per hour (ACFH) is not allowed to exceed design value (case 1 value). In all cases reduction in the steam to carbon ratio more than offsets the gas flow increase associated with the increased natural gas rates and higher ATR exit temperatures (see flow rate of gas at ATR exit in ACFH.) In all cases the $CO_2$ removal system would have to be oversized versus operations when the gasifier is operational (see flow rates at $CO_2$ removal unit inlet and outlet).

Because of the ability to run the ATR at lower steam to carbon ratios the methanol output is maintained at about design production rate of 5004 tonnes/d, and the $(H_2-CO_2)/(CO+CO_2)$ ratio is maintained at or near the preferred values when the coal gasifier is not operational or at part capacity.

For cases where methanol is the desired product from liquid fuel production unit 8, there may be an accompanying downstream process (not shown) that converts methanol to gasoline. All or a portion of the liquefied petroleum gases (LPG) generated as a byproduct from the conversion of methanol to gasoline can be fed to the light fossil fuel conversion unit.

TABLE 1

|  | Case 1 | Case 2 | Case 3 |
|---|---|---|---|
| Liquid fuel product (Methanol), tonnes/d | 5004 | 5002 | 5000 |
| Gasification Unit 2: | | | |
| Operating capacity | 100% | 0% | 50% |
| Oxygen 12 flow, Tons/d | 1400 | 0 | 700 |
| Solid feedstock 10 (Pitt #8 coal), Tons/d | 1590 | 0 | 795 |
| Gasifier-syngas 26: | | | |
| Flow, MMSCFD | 102 | — | 51 |
| $H_2/CO$ ratio | 0.5 | — | 0.5 |
| Light Fossil fuel conversion unit 6 | ATR | ATR | ATR |
| Configuration: | | | |
| NG 18 | 111.8 | 147.3 | 128.5 |
| Oxygen 16 flow, tons/d | 2546 | 3402 | 2992 |
| Steam to carbon ratio | 2.8 | 0.6 | 1.4 |
| Pre-reform feed T, ° F. | 1000 | 1000 | 1000 |
| ATR exit T, ° F. | 1650 | 1900 | 1800 |
| Gas flow @ ATR exit, MMACFH | 4.08 | 3.71 | 3.81 |
| Gas flow 27 at $CO_2$ removal unit inlet, MMSCFD | 361 | 431 | 394 |
| Gas flow 28 at $CO_2$ removal unit exit, MMSCFD | 328 | 430 | 377 |
| $H_2$-rich syngas 28 | | | |
| Composition (mol %): | | | |
| $H_2$ | 75.7 | 65.7 | 70 |
| CO | 17.3 | 28 | 23.6 |
| $CO_2$ | 5.3 | 4.8 | 5 |
| Other - $N_2$, $H_2O$, Ar, etc. | 1.7 | 1.5 | 1.4 |
| $H_2/CO$ ratio | 4.4 | 2.3 | 3 |
| Liquid fuel production unit 8 | | | |
| Syngas Feed 30: | | | |
| Flow, MMSCFD | 430 | 430 | 428 |
| Composition, mol % | | | |
| $H_2$ | 65.4 | 65.7 | 65.5 |
| CO | 28.2 | 28 | 28.4 |
| $CO_2$ | 4.8 | 4.8 | 4.8 |
| Other - $N_2$, $H_2O$, Ar, etc. | 1.6 | 1.5 | 1.2 |
| $H_2/CO$ ratio | 2.3 | 2.3 | 2.5 |
| $(H_2-CO_2)/(CO+CO_2)$ | 2.01 | 2.05 | 2 |

Example 2

Fischer Tropsch Liquid Fuels Production Hybrid Plant

In this example the hybrid plant and light fossil fuel conversion unit configurations shown in FIGS. 1 and 2 are simulated to produce Fischer-Tropsch (FT) liquids as liquid fuel product. Table 2 lists the operating modes and simulation results. In case 4 (design case) the hybrid plant design production rate is equivalent to about 17,000 barrels/day of Fischer-Tropsch (FT) liquids fuel product (diesel plus naphtha). The gasification unit processes a little more than 2,500 tons/d of coal and consumes 2264 tons/d of oxygen to produce 163.8 MMSCFD gasifier-syngas having a hydrogen to carbon monoxide ratio of 0.5. The ATR is operated at a steam to carbon ratio of 1.8 using 3736 tons/d oxygen to convert natural gas and provide 74% hydrogen plus carbon monoxide and 50% carbon monoxide in feed to the FT liquids fuel production unit 8.

When the gasification unit is not available there are a number of possible modes for operating the ATR to maintain the liquid fuel production at desired rate. Adjustments in light fossil fuel feed flow, oxygen feed flow, $CO_2$ recycle, and/or ratio of steam to carbon in the light fossil fuel conversion unit when the gasifier is not operational (or operating at reduced capacity) compared to when gasifier is fully operational can be carried out such that the flow rate of gas at ATR exit in actual cubic feet per hour (ACFH) does not exceed design value. To take full utilization of the ATR capability it is anticipated that the flow rate of gas leaving the ATR expressed in actual cubic feet per hour (ACFH) should be the same, irrespective of whether gasifier is operational or not. This scenario (case 5) increases light fossil fuel feed to ATR, diverts oxygen from gasification unit (45% of design value) to ATR, decreases steam to carbon ratio to 0.6, recycles $CO_2$ to ATR and produces FT liquids fuel product at about 90% of the design production rate. In this scenario the $CO_2$ removal unit would need a capacity that is about 17% larger than the design with the gasifier running.

Based on the air separation unit capacity 100% of the liquid fuel production rate (design value) is possible, however the ATR and the entire system used to generate $H_2$-rich syngas from natural gas would need to be oversized. This is not likely to be economical since the gasification unit will not be available for only 10% to 15% of the year.

$H_2$-rich syngas produced at 1900° F. with steam to carbon ratio of 0.6 and near complete recycle of captured $CO_2$ has significant differences in composition relative to the $H_2$-rich syngas produced at 1700° F. with steam to carbon ratio of 1.8 and without recycle of any captured $CO_2$. For example the $H_2$:CO ratio is reduced from about 3.3 to about 1.9, closer to the optimum $H_2$:CO ratio of about 2.0 for liquid fuel synthesis.

Case 6 shows the expected plant capacity if the $CO_2$ removal unit's capacity limits the gas flow (same flow capacity as when gasifier is operational). In this scenario light fossil fuel feed to ATR is increased, portion of gasification unit oxygen (about 14% of design value) is diverted to ATR, steam to carbon ratio is decreased to 0.6, $CO_2$ is recycled to ATR, thus producing FT liquids fuel product at about 77% of the design production rate.

TABLE 2

|  | Case 4 | Case 5 | Case 6 |
|---|---|---|---|
| Liquid fuel product (F-T Synthetic Crude), % capacity* | 100 | 90 | 77 |
| Gasification Unit 2: | | | |
| Operational | Yes | No | No |
| Oxygen 12 flow, Tons/d | 2264 | 0 | 0 |
| Solid feedstock 10, Pitt #8, Tons/d | 2571 | 0 | 0 |
| Gasifier-syngas 26: | | | |
| Flow, MMSCFD | 164 | | |
| $H_2$/CO ratio | 0.5 | — | — |
| Light fossil fuel conversion unit 6 Configuration | ATR | ATR | ATR |
| NG 18, MMBtu/d(LHV) | 147,197 | 181,620 | 155,422 |
| Oxygen 16, Tons/d | 3736 | 4750 | 4060 |
| $CO_2$ recycle, Tons/d | 0 | 1864 | 1595 |
| Steam to carbon ratio | 1.8 | 0.6 | 0.6 |
| Pre-reform feed T, ° F. | 1000 | 1000 | 1000 |
| ATR exit T, ° F. | 1750 | 1900 | 1900 |
| Gas flow @ ATR exit, MMACFH | 5.11 | 5.11 | 4.37 |
| Gas flow 27 @ $CO_2$ removal unit inlet, MMSCFD | 504 | 588 | 504 |
| Gas flow 28 @ $CO_2$ removal unit exit, MMSCFD | 470 | 556 | 476 |
| Stream 28 Composition (mol %): | | | |
| $H_2$ | 72.4 | 64.1 | 64.1 |
| CO | 21.8 | 33.5 | 33.5 |
| $CO_2$ | 4.3 | 1 | 1 |
| Other - $N_2$, $H_2O$, Ar, etc. | 1.5 | 1.4 | 1.4 |
| $H_2$/CO ratio | 3.3 | 1.9 | 1.9 |
| Liquid fuel production unit 8 | | | |
| Syngas Feed 30: | | | |
| Flow, MMSCFD | 634 | 556 | 476 |
| Composition, mol % | | | |
| $H_2$ | 62 | 64.1 | 64.1 |
| CO | 32.6 | 33.5 | 33.5 |
| $CO_2$ | 4 | 1 | 1 |
| Other - $N_2$, $H_2O$, Ar, etc. | 1.4 | 1.4 | 1.4 |
| $H_2$/CO ratio | 1.9 | 1.9 | 1.9 |

*100% corresponds to 17,000 BBL/d of crude FT liquids

Example 3

Methanol Production Hybrid Plant

In this case the light fossil fuel conversion unit contains a SMR coupled to a downstream autothermal reformer (FIG. 3). During normal operation, i.e. gasification unit is fully operational, the SMR and ATR(SMR-ATR) is operated with the SMR process gas exit temperature at about 1550° F. to about 1600° F. The ATR could be in a standby condition (little or no oxygen addition) or operated with sufficient oxygen addition to raise the gas temperature to the normal ATR exit temperature of about 1750° F. to 1900° F.

When the gasification unit is operating at reduced capacity or is not operational then less than design quantity of oxygen is needed in the gasification unit. The oxygen from air separation plant that would have been fed to the gasification unit becomes available. At least some of this available oxygen can be routed to light fossil fuel conversion unit to increase oxygen feed to ATR. To maintain liquid fuel production at a desired rate, flow of light fossil fuel feed to the SMR is increased to produce more $H_2$-rich syngas and compensate for reduced gasifier-syngas flow available from the gasification unit. Several choices are available on how to operate the SMR. For example, the SMR at higher flow rate of light fossil fuel feed can be operated with or without further increase in heat input (firing duty). If operated without increase in heat input then the exit temperature of the SMR process gas will drop; methane conversion will decrease causing more unconverted methane to leave SMR. If one decides to operate the SMR with increased heat input, there may be limitations on the allowable increase in heat input for e.g. due to maximum catalyst tube wall temperature constraint. If the increase in heat input is not adequate then the exit temperature of the SMR process gas could drop and the SMR process gas contains relatively more unconverted methane. The SMR at higher flow rate of light fossil fuel feed can also be operated such that the steam input to SMR may or may not be increased. Consequently, the steam to carbon (S/C) ratio will remain at design value or differ, and could affect the SMR process gas composition and temperature. In the SMR and ATR configuration, the process gas leaving SMR serves as feed to the ATR. There are several choices available on how to operate the ATR. For example, the oxygen originally supplied to the gasifier is now available for use in the ATR. Oxygen fed to ATR assists in converting methane in the SMR exit (ATR feed) to synthesis gas at desired temperature, for example about 1800° F. The synthesis gas flow rate can be 100% larger than that attainable from SMR alone.

Synthesis gas leaving ATR at 1800° F. has significant differences compared to synthesis gas at 1550-1600° F. For example methane content is reduced from the 4 mole % to 6 mole % range (on a dry basis) at the lower temperature to less than 1 mole % (on a dry basis) at 1800° F. The hydrogen to carbon monoxide ($H_2$:CO) ratio is reduced from about 4.5 at lower temperature to about 3.5 at 1800° F.

Adding $CO_2$ to the feed to the SMR-ATR combination can further reduce the $H_2$:CO ratio, for example in the 2.5-3.0 range.

A world scale methanol facility containing process units shown in FIGS. 1 and 3 is simulated. The first column in Table 3 summarizes results for design conditions (case 7), producing methanol at a design production rate of 5002 tonnes/d. The light fossil fuel conversion unit (SMR+ATR combination) provides 71% hydrogen plus carbon monoxide and 47% carbon monoxide in feed to the liquid fuel production unit. The second column in Table 3 (case 8) summarizes results when gasifier is not operational and all available oxygen is diverted to ATR. Two adjustments are made to the SMR operations; natural gas feed flow is increased and steam to carbon ratio decreased from 2.8 in case 7 (design case) to 2 in case 8. Resulting SMR product gas 642 is processed in ATR 604 using higher oxygen flow and recycling $CO_2$ to ATR. The ratio of $H_2$:CO is decreased from 4.4 at design conditions (case 7) to 3.0 in case 8, and the ratio of $(H_2-CO_2)/(CO+CO_2)$ is increased from 2.00 to 2.35. Assuming the $CO_2$ removal unit is oversized (flow rate of gas 27 is higher than in design case) the hybrid plant liquid fuel production rate is constrained in case 8 (gasification unit not operational) by the amount of oxygen available for feeding to the light fossil fuel conversion unit 6. All the oxygen used for the coal gasification unit is sent to the ATR. The net impact is that almost 95% of the full plant output is achievable when the gasifier is not operational. Increasing the output to 100% of full plant output would require an air separation unit that has slightly more capacity than that used in this design. A membrane could be used to reduce the $(H_2-CO_2)/(CO+CO_2)$ ratio to the 2.0-2.1 range normally required for feeds to methanol synthesis loop.

TABLE 3

|  | Case 7 | Case 8 |
| --- | --- | --- |
| Liquid fuel product (Methanol), tonnes/d | 5002 | 4748 |
| Gasification Unit 2: | | |
| Operational | Yes | No |
| Oxygen 12 flow, Tons/d | 1400 | 0 |
| Solid feedstock 10, Pitt #8 Coal, Tons/d | 1590 | 0 |
| Gasifier-syngas 26: | | |
| Flow, MMSCFD | 101.3 | — |
| $H_2$/CO ratio | 0.5 | |
| Light Fossil fuel conversion unit 6 Configuration: | SMR + ATR | SMR + ATR |
| Total NG 18, MMSCFD | 124.8 | 158.6 |
| NG feed 618 | | |
| NG fuel 644 | | |
| Oxygen 16, Tons/d | 380 | 1780 |
| $CO_2$ recycled, tons/d | 168 | 1000 |
| Steam to carbon ratio | 2.8 | 2 |
| Pre-reform feed T, ° F. | 1000 | 1000 |
| SMR exit T, ° F. | 1575 | 1446 |
| ATR exit T, ° F. | 1700 | 1900 |
| ATR product flow @ ATR exit, MMACFH | 3.82 | 3.67 |
| Gas 27 to $CO_2$ removal unit, MMSCFD | 338 | 469 |
| Stream 28: | | |
| Flow, MMSCFD | 328 | 453 |
| Composition, mol % | | |
| $H_2$ | 75.4 | 71.1 |
| CO | 17.3 | 23.9 |
| $CO_2$ | 5.3 | 4.5 |

TABLE 3-continued

|  | Case 7 | Case 8 |
| --- | --- | --- |
| Other - $N_2$, $H_2O$, Ar, etc. | 2.0 | 0.5 |
| $H_2$/CO ratio | 4.4 | 3 |
| Liquid Fuel Production Unit 8 Syngas Feed 30 | | |
| Flow, MMSCFD | 429 | 453 |
| Composition, mol % | | |
| $H_2$ | 65.1 | 71.1 |
| CO | 28.3 | 23.9 |
| $CO_2$ | 4.8 | 4.5 |
| Other - $N_2$, $H_2O$, Ar, etc. | 1.8 | 0.5 |
| $H_2$/CO ratio | 2.3 | 3.0 |
| $(H_2 - CO_2)/(CO + CO_2)$ after $H_2$ recycle | 2 | 2.35* |

*No $H_2$ recycle

Example 4

Methanol Production Hybrid Plant

In this example during normal operation, feed to liquid fuel production unit 8 is provided by gasification of biomass in unit 2 and light fossil fuel conversion unit 6 containing SMR and ATR (FIG. 3). Feeds to SMR 602 include natural gas 618 and steam 624, and feeds to ATR 604 include SMR product gas 642 and oxygen 16. Simulation results for four operating modes are summarized in Table 4.

In the first operating mode, design case (case 9), the gasification unit 2 gasifies a solid biomass feedstock to produce gasifier-syngas 26 that has a hydrogen to carbon monoxide ratio of 0.87. The SMR 602 is operated at a steam to carbon ration of 2.8 and a $CO_2$ recycle of 1270 tons/day with sufficient energy input to carry out reforming and water gas shift reactions to equilibration at SMR outlet temperature of 1575° F. The gas 642 leaving SMR 602 is passed through ATR 604 that uses minimal oxygen to maintain ATR catalyst bed at temperature in standby operating mode. $H_2$-rich syngas 28 leaving the light fossil fuel conversion unit 2 has a $H_2$:CO ratio of 3.24. $H_2$-rich syngas stream 28 and gasifier-syngas stream 26 are mixed to form mixed syngas stream 30 that has a $H_2$:CO ratio of 2.22. Stream 28 provides 75% hydrogen plus carbon monoxide and 57% carbon monoxide in mixed syngas stream 30. The mixed syngas stream 30 is processed in liquid fuel production unit 8 to produce methanol at a design production rate of 1139 tonnes/day of methanol.

In the second operating mode (case 10) gasification unit 2 is not operational. Further, no oxygen is supplied to ATR. If the SMR were to maintain operations as normal (case 9 conditions), the output of methanol reactor would drop to about 57% of that achieved when the plant is operating in combination with the gasifier.

In the third operating mode (case 11) gasification unit 2 is not operational. The light fossil fuel conversion unit 6 operations are adjusted to increase $H_2$-rich syngas 28 production rate. The light fossil fuel feed flow 618 is increased. Oxygen that would have been supplied to the gasification unit, 343 tons/d and now available is routed to ATR. The steam to carbon ratio is maintained at 2.8, same as design case (case 9). The $CO_2$ recycle is 1291 tons/day. These adjustments increase flow rate of $H_2$-rich syngas 28, the $H_2$:CO ratio decreases from 3.24 in case 9 to 2.64 in case 11, and the CO available for methanol synthesis increases by more than 60%. The resulting methanol production would be nearly 92% of the case when the gasifier is operational.

In the fourth operating mode (case 12) also the gasification unit 2 is not operational. The light fossil fuel feed flow is increased. 343 tons/d of oxygen that would have been supplied to the gasification unit are now available and fed to the ATR. The flow of steam is adjusted to decrease steam to carbon ratio from design value of 2.8 to 2.0. 1198 tons/day of $CO_2$ is recycled to ATR. These adjustments increase methanol output to near design capacity. Since gasifier outages can last a month or more this ability to maintain plant nameplate capacity when the gasifier is unavailable will have a major impact on the income to the project.

The design of methanol reactors are optimized by maintaining the ratio $(H_2—CO_2)/(CO+CO_2)$ in the range of 2.0 to 2.1. The design with the gasifier operational is in the middle of that range. The performance of the cases with gasifier not operational would be improved had the ratio been closer to the design range. $CO_2$ in stream 27 can be captured (FIG. 1) and recycled to light fossil fuel conversion unit 6 as a means for managing the $H_2$:CO ratio in the feed to the liquid fuel production unit 8. The recycled $CO_2$ can be added directly to ATR, either separately or mixed with oxygen.

TABLE 4

|  | Case 9 | Case 10 | Case 11 | Case 12 |
| --- | --- | --- | --- | --- |
| Liquid fuel prod. (Methanol) Gallons/hr (Tonnes/d) | 15857 (1139) | 9068 (651) | 14559 (1046) | 15600 (1120) |
| Gasification Unit 2: |  |  |  |  |
| Operational | Yes (at 100%) | No | No | No |
| Solid feed stock 10, dry tons/day | 900 | — | — | — |
| Oxygen 12 flow, Tons/d | 343 | — | — | — |
| Gasifier-syngas 26: |  |  |  |  |
| $H_2$, lbmol/h | 1296 | — | — | — |
| CO, lbmol/h | 1482 | — | — | — |
| $CO_2$, lbmol/h | 54 | — | — | — |
| $H_2$/CO ratio | 0.87 | — | — | — |
| Light fossil fuel conversion unit 6 Configuration: | SMR + ATR | SMR + ATR | SMR + ATR | SMR + ATR |
| Total NG 18 |  |  |  |  |
| NG feed 618, lbmol/h | 2620 | 2620 | 3387 | 3628 |
| NG fuel 644, MMBtu (HHV)/h | 474 | 474 | 457 | 458 |
| Lbmol/hr | 1250 | 1250 | 1205 | 1208 |
| Oxygen 16, tons/d | 0 | 0 | 343 | 343 |
| $CO_2$ recycled, tons/d | 1270 | 1270 | 1291 | 1198 |
| Steam to carbon ratio | 2.8 | 2.8 | 2.8 | 2 |
| SMR exit T, ° F. | 1575 | 1575 | 1461 | 1498 |
| ATR exit T, ° F. | 1575 | N/A | 1790 | 1790 |
| Stream 28: |  |  |  |  |
| $H_2$, lbmol/h | 6365 | 6365 | 8364 | 8794 |
| CO, lbmol/h | 1964 | 1964 | 3173 | 3391 |
| $CO_2$, lbmol/h | 141 | 141 | 77 | 125 |
| $H_2$/CO ratio | 3.24 | 3.24 | 2.64 | 2.59 |
| Liquid fuel production unit 8 Syngas Feed 30 |  |  |  |  |
| $H_2$, lbmol/h | 7660 | 6365 | 8364 | 8794 |
| CO, lbmol/h | 3446 | 1964 | 3173 | 3391 |
| $CO_2$, lbmol/h | 195 | 141 | 77 | 125 |
| $H_2$/CO ratio | 2.22 | 3.24 | 2.64 | 2.59 |
| $(H_2 - CO_2)/(CO + CO_2)$ | 2.05 | 2.96 | 2.55 | 2.47 |

While the invention has been described in detail with reference to specific embodiments thereof, it will become apparent to one skilled in the art that various changes and modifications can be made and equivalents employed, without departing from the scope of the appended claims.

What is claimed is:

1. A method of operating a hybrid plant, where a gasification unit in the hybrid plant is operating at less than its design capacity or is not operational, comprising:

a) increasing a light fossil fuel feed to a light fossil fuel conversion unit of the hybrid plant;

b) increasing oxygen input to an autothermal reformer in said fossil fuel conversion unit by diverting at least a portion of oxygen that would have been fed to said gasification unit, conditioned on the autothermal reformer temperature and exiting volumetric gas flow not to exceed a design value;

c) decreasing said light fossil fuel conversion unit steam to carbon ratio, and d) producing a liquid fuel product at a production rate between 70% to 110% of the hybrid plant design production rate.

2. A method according to claim 1, wherein at least 10% of the oxygen that would have been fed to said gasification unit is diverted to said light fossil fuel conversion unit.

3. A method according to claim 1, wherein the steam to carbon ratio in step (c) is greater than 0.4.

4. A method according to claim 1, wherein the additional light fossil fuel feed to the light fossil fuel conversion unit in step (a) is introduced into an autothermal reformer in the light fossil fuel conversion unit.

5. A method according to claim 1, wherein the additional light fossil fuel feed to the light fossil fuel conversion unit in step (a) is introduced into a steam methane reformer coupled to a downstream autothermal reformer in the light fossil fuel conversion unit.

6. A method according to claim 1, wherein the additional light fossil fuel feed to the light fossil fuel conversion unit in step (a) is divided into two streams, where the first stream is fed to a steam methane reformer coupled to a downstream autothermal reformer in the light fossil fuel conversion unit and the second stream is fed directly to said downstream autothermal reformer.

7. A method according to claim 1, wherein a hydrogen and carbon monoxide containing $H_2$— rich syngas produced in the light fossil fuel conversion unit is further treated to recover a hydrogen product.

8. A method according to claim 1, wherein oxygen input diverted from the gasification unit to the light fossil fuel conversion unit is from an air separation unit within the hybrid plant or from an air separation unit external to the hybrid plant.

9. A method according to claim 1, wherein a $CO_2$ stream is recycled from a $CO_2$ removal unit in the hybrid plant to the autothermal reformer.

10. A method according to claim 1, wherein a $CO_2$ stream is recycled from a $CO_2$ removal unit in the hybrid plant to a steam methane reformer in the light fossil fuel conversion unit.

11. A method according to claim 1, wherein a $CO_2$ stream is recycled from a $CO_2$ removal unit in the hybrid plant to both, a steam methane reformer coupled to a downstream autothermal reformer in the light fossil fuel conversion unit and to said downstream autothermal reformer.

12. A method according to claim 9, wherein a hydrogen and carbon monoxide containing $H_2$— rich syngas flow exiting said $CO_2$ removal unit does not exceed a design value.

\* \* \* \* \*